(12) United States Patent
Rijken et al.

(10) Patent No.: US 6,305,083 B1
(45) Date of Patent: Oct. 23, 2001

(54) APPARATUS WITH A HOUSING PROVIDED WITH A SYNTHETIC RESIN WALL PORTION WITH A SYNTHETIC RESIN PANEL PROVIDED THEREON

(75) Inventors: Martinus M. Rijken, Drachten; Matthijs J. Meijer, Eindhoven, both of (NL)

(73) Assignee: U.S. Philips Corporation, New York, NY (US)

( * ) Notice: Subject to any disclaimer, the term of this patent is extended or adjusted under 35 U.S.C. 154(b) by 0 days.

(21) Appl. No.: 09/422,739

(22) Filed: Oct. 21, 1999

(30) Foreign Application Priority Data

Oct. 23, 1998 (EP) .................................................. 98203584

(51) Int. Cl.⁷ ...................................................... B26B 19/14
(52) U.S. Cl. ......................................... 30/43.6; 156/274.4
(58) Field of Search .................................... 30/43.6, 43.5, 30/43.4, 43.9, 43.92; 156/274.4

(56) References Cited

U.S. PATENT DOCUMENTS 4,801,343    1/1989   Tamba et al. .......................... 156/69

5,483,745  *  1/1996   Izumi .................................... 30/43.6

* cited by examiner

Primary Examiner—Douglas D. Watts
(74) Attorney, Agent, or Firm—Ernestine C. Bartlett; Norman N. Spain

(57) ABSTRACT

A housing (1) of an apparatus has a plastics wall portion (2) provided with a plastics panel (4). To make a reliable and visually acceptable connection of the panel (4) to the wall portion (2), the panel is fixed to the wall portion by means of an induction welding process. In this way the connection is resistant to chemical compounds like lotions. Therefore a metal element (8) of electric conducting material having the shape of a closed loop wire is inserted between the wall portion (2) and the panel (4) and subsequently an electromagnetic field is applied in close proximity to the element. Preferably such panel (4) can be used to cover an opening (11) in the wall portion (2) for a display (10) and/or a switch (15) function. To make the housing watertight the element (8) between the panel (4) and the wall portion (2) should surround the opening (3,11).

8 Claims, 4 Drawing Sheets

APPARATUS WITH A HOUSING PROVIDED WITH A SYNTHETIC RESIN WALL PORTION WITH A SYNTHETIC RESIN PANEL PROVIDED THEREON

BACKGROUND OF THE INVENTION

The invention relates to an apparatus, such as a shaver, a toothbrush, or a kitchen machine, with a housing which has a synthetic resin wall portion on which a synthetic resin panel is fastened.

It is often desirable for wall portions of a housing to be provided with panels. Such panels may have a decorative function, but also a technical function. Various methods are known for fastening such panels to a housing wall. Examples are screw connections and snap connections. If the panel is present at the outside of the wall portion, the above methods do not lead to an attractive appearance. Snapping home in practice often gives rise to play, so that the panel will be slightly loose. Gluing is a better method in this case. Although there are satisfactory glue compositions nowadays, they are not resistant to chemical substances such as additives (lotions) in the long run. Another fastening method is ultrasonic welding. Here a vibratory force is applied to one of the parts by means of a tool. This often causes damage to the surface of the wall, which is not acceptable visually. In addition, the choice of materials is limited in the case of ultrasonic welding, inter alias on account of the material characteristics.

SUMMARY OF THE INVENTION

It is an object of the invention to provide an apparatus in which a synthetic resin panel is fastened to a synthetic resin wall portion of a housing in a reliable and visually acceptable manner.

The invention is for this purpose characterized in that an element of electrically conducting material having the shape of a closed loop is present between the panel and the wall portion, by means of which element the panel is fastened to the wall portion through an RF (Radio Frequency) adhesion process. In an RF (Radio Frequency) adhesion process, also called inductive welding, an electromagnetic field is generated close to the element, so that an induction current will flow through the element. The ohmic resistance of the element causes a heat generation in the element which melts the synthetic resin parts adjacent to the elements, whereupon these elements are fused together and fused to the element upon cooling down. Melting takes place through a small depth, so that no deformations are visible at the surface of the synthetic resin panel. It was found that this method leads to a reliable connection of the panel to the wall portion which is visually acceptable and is resistant to liquids, especially chemical liquids. An additional advantage of this method is that the element need not be plane but may also have a curved shape, adapted to the shape of the wall portion and the panel. This offers a designer a considerable freedom in design.

A preferred embodiment is characterized in that the synthetic resin housing is at least partly watertight, and the wall portion has at least one opening for accommodating electrical or mechanical elements, such as a display or a switch, while the panel is arranged over said opening and the element of electrically conducting material encircles the opening. If the synthetic resin wall portion of the housing is provided with an opening and the housing has to be watertight for cleaning purposes, the opening must also be closed in a watertight manner. The most well-known method for rendering the opening with a panel watertight is through the application of an elastic seal between the panel and the wall portion. The parts must then be fastened against one another with force, for example with screws. This is a good method in principle, but it is found in practice that the seal may lose its elasticity after a longer period, and thus its sealing effect, also through the action of chemical substances. Nowadays, the seal is integrally manufactured with one of the synthetic resin parts in the injection molding process. This leads to another problem if at least one of the parts is to be painted. The painting process must take place before electrical or mechanical components are fastened in or against the housing wall. It is not possible, however, to injection-mold a sealing to painted parts. As was mentioned earlier, a glue connection and ultrasonic welding also have their disadvantages. The joint obtained through inductive welding supplies a highly reliable seal.

A further embodiment is characterized in that the wall portion is provided with two openings, one opening for a display and the other opening for a switch, said openings being both covered at an inside of the wall portion by said panel, the latter being provided with a window of a transparent material situated in front of the display opening and with a membrane with an actuator situated in the opening for the switch.

A yet further embodiment is characterized in that a second panel is present which is fastened to the outside of the wall portion, again by means of an element of electrically conducting material in the shape of a closed loop and an RF adhesion process, which panel has an operational surface of a flexible material which lies opposite the membrane with the actuator of the panel mentioned earlier, and which panel covers the opening in the wall portion in front of the switch.

BRIEF DESCRIPTION OF THE DRAWINGS

The invention will now be explained in more detail with reference to an example shown in a drawing, in which.

DESCRIPTION OF THE PREFERRED EMBODIMENTS

Figure 1:
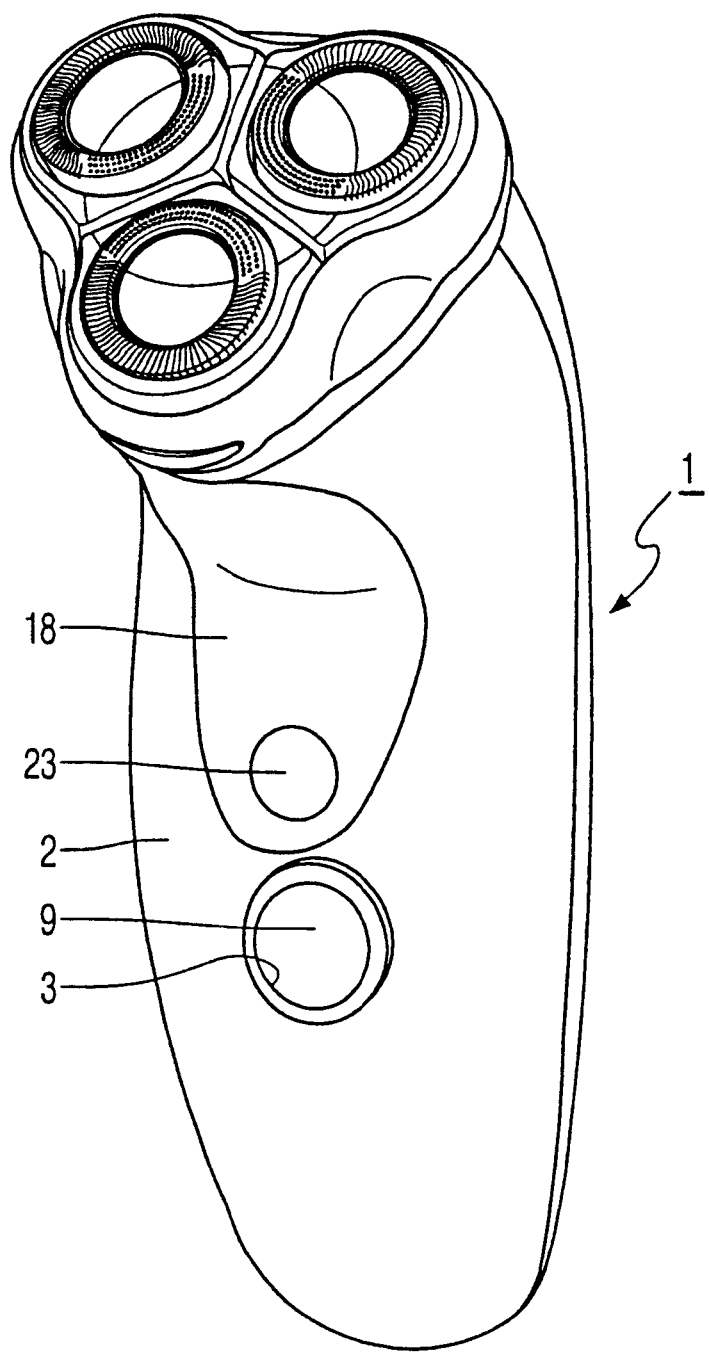
FIG. 1 shows an electric shaver in perspective view.
Figure 2:
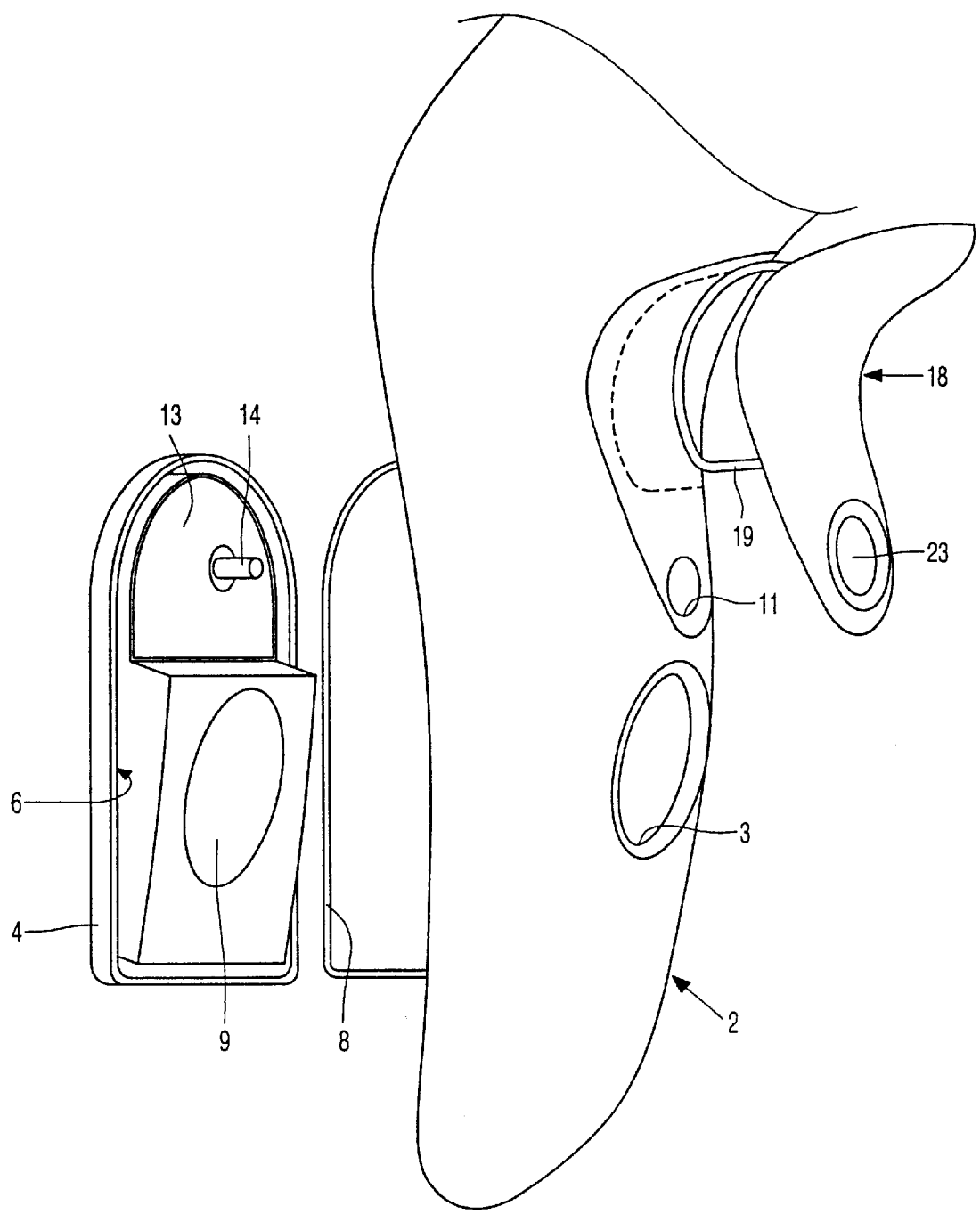
FIG. 2 shows part of the shaver of FIG. 1, some parts being represented in exploded view.
Figure 3:
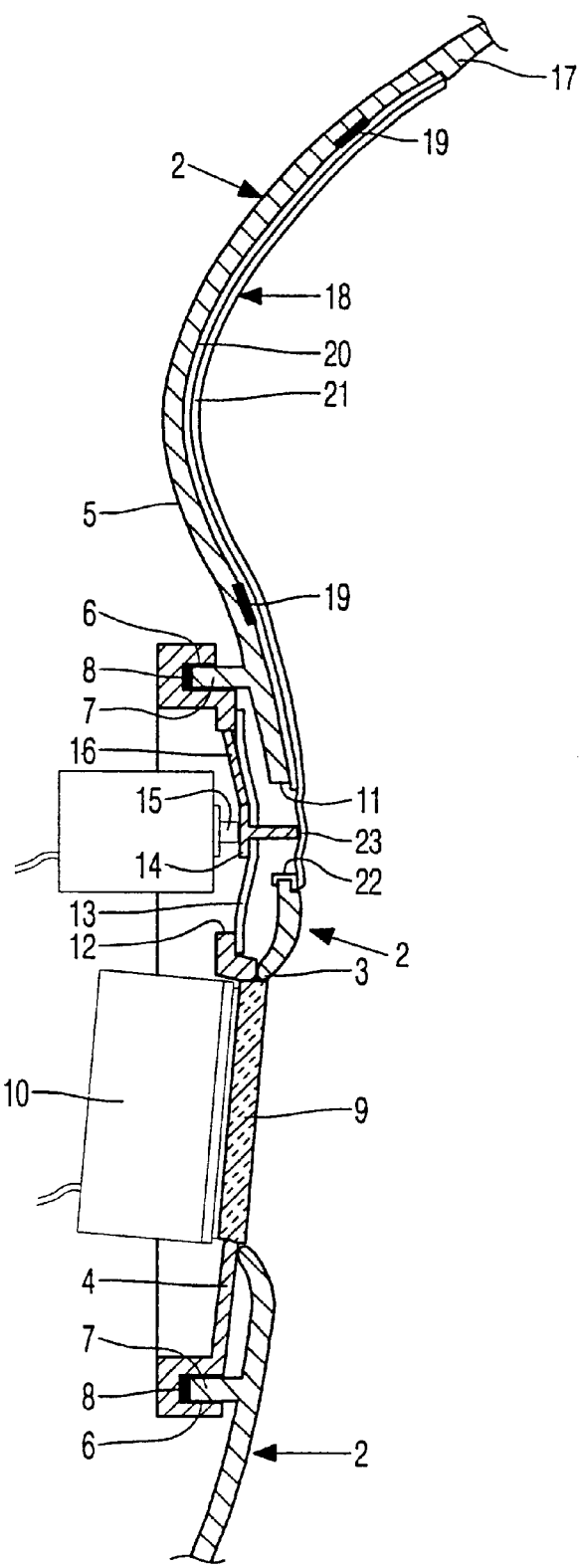
FIG. 3 is a cross-sectional view of part of the shaver of FIG. 1.

The electric shaver has a housing 1 with a synthetic resin wall portion 2 in which an opening 3 is present to accommodate a display function. The opening is closed off by means of a synthetic resin panel 4 which is fastened against the inside 5 of the wall portion 2. The panel 4 is for this purpose provided with a circumferential groove 6, while the inside of the wall portion is provided with a raised wall 7 which fits the groove 6. The raised wall and the groove together encircle the opening 3. Between the groove 6 and the raised wall 7 there is an element 8 of an electrically conducting material which has the shape of a closed loop corresponding to the shape of the bottom of the groove 6. The element 8 is preferably made of brass because of its suitable resistivity value. Obviously, however, alternative materials are also possible. Upon the application of an electromagnetic field adjacent the element 6, a current will flow through this element causing a heat generation which melts the synthetic resin parts of the groove 6 and of the raised wall 7, which parts will become fused together through cooling-down after the electromagnetic field has been removed. The element 8 remains fixed in its connection location. The panel 4 thus closes off the opening 3 in a watertight manner. The opening is designed for holding a display in this example. The panel 4 is for this purpose provided with a window 9 of a transparent material. Behind this window there is an electronic component such as an LCD 10. The wall portion 2 is further provided with a second opening 11 designed for accommodating a switch. The covering panel 4 also covers this opening 11, i.e. the current-conducting element 8 between the groove 6 of the panel 4 and the raised wall 7 of the wall portion 2 also surrounds the opening 11. The panel 4 is provided with an opening 12 for a switch closed off in a watertight manner by a membrane 13. An actuator 14, by means of which a switch 15 is operated, for example for switching the apparatus on and off, is present in the center of the membrane. The actuator 14 may be molded together with the synthetic resin panel 4 in the injection molding process in the form of a thin, flexible synthetic resin strip 16. The actuator is passed through the opening 12. The opening 12 is covered at the outside 17 of the wall portion 2 by a second panel 18 which is also fastened to the wall portion 2 in an RF adhesion process. To this end, an element 19 of electrically conducting material and having the shape of a closed loop is applied between the panel 18 and the outside 17 of the wall portion 2. The panel 18 comprises two layers, i.e. a first layer 20, for example made of the same type of synthetic resin as the wall portion 2, and a second layer 21 of a flexible synthetic resin. The first layer 20 has an opening 22 covered by the flexible second layer at the area of the opening 11. The actuator 14 is present immediately behind the flexible layer 21. This portion of the flexible layer accordingly acts as an operational surface 23. Applying a pressure on the flexible operational surface presses down the actuator, which thus operates the switch 15. The panel 18 at the same time serves as a decorative panel. The flexible layer 21 in addition provides a secure grip when the apparatus is held.

Figure 4:
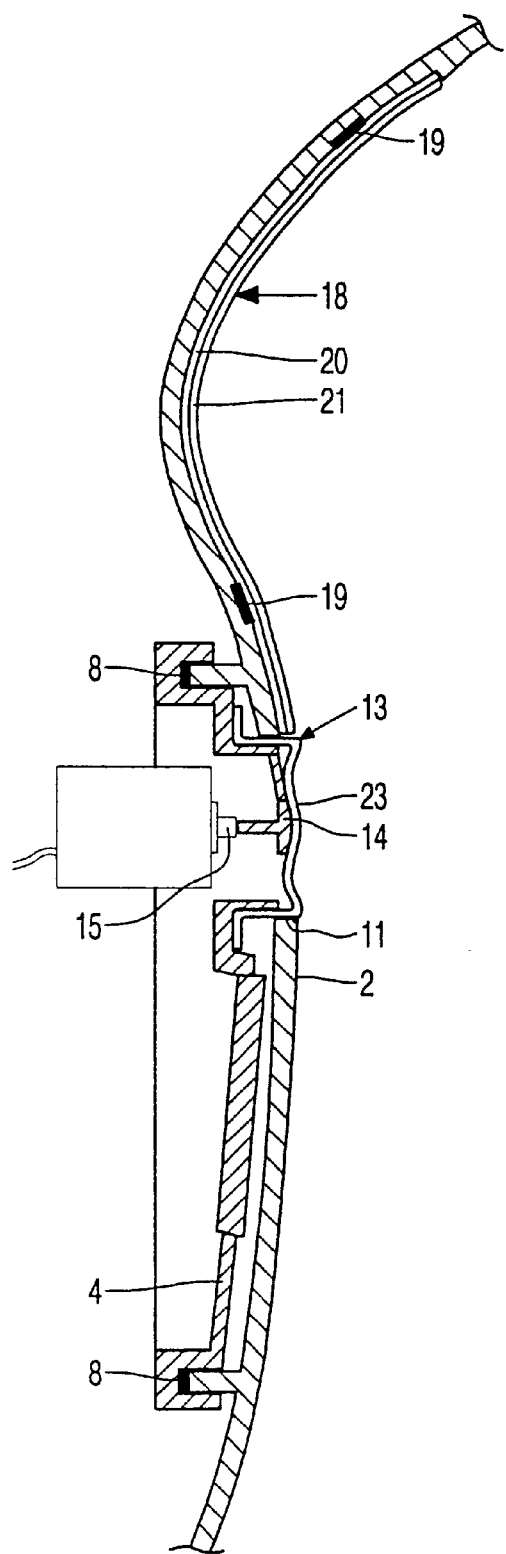
FIG. 4 is a cross-sectional view of part of the shaver of FIG. 1 in a second embodiment.

In the second embodiment shown in FIG. 4, the membrane 13 extends into the opening 11 of the wall portion 2 and forms one integral whole with the operational surface 23 for the switch 15. The second panel 18 here only has a decorative function and the function of providing a secure grip thanks to the flexible layer 21.

The RF adhesion process, also called induction welding process, takes place at a low frequency, i.e. approximately 40 kHz. Nickel or brass is used as the material for the element 8, 19.

It will be obvious that the invention may also find an application in other apparatuses which must be watertight such as a toothbrush or a kitchen machine.

The elements 8, 19 need not lie in a flat plane, but they may also have a curved shape, such as the element 19. This means for a designer that he has a greater freedom in the choice of component shapes. The elements are simple and inexpensive stamping products. Much waste material is left after stamping, but this may be easily recycled.

What is claimed is:

1. An apparatus, such as a shaver, a toothbrush, or a kitchen machine, with a housing (1) which is at least partially watertight and which housing has a synthetic resin wall portion (2) on which a synthetic resin panel (4) is fastened, wherein the wall portion (2) has an opening (11) for accommodating a switch (15), the panel (4) is fastened to the wall portion (2) in an RF adhesion process and the panel (2) has an opening which is closed off by a membrane (13), which membrane is provided with an actuator (14) which is present in the opening (11) for the switch (15).

2. An apparatus, such as a shaver, toothbrush or a kitchen machine, with a housing (1) which is at least partially water tight and which housing has a synthetic resin wall portion (2) on which a synthetic resin panel (4) is fastened, wherein the wall portion (2) has a first opening (3) for accommodating a display and a second opening (11) for accommodating a switch (15), the opening (3) for the display and a second opening (11) for the switch both covered at an inside 95) of the wall portion (2) by said panel (4), said panel (4) being provided with a window (9) of a transparent material situated in front of the opening (3) for the display and with a membrane (13) with an actuator (14) situated in the opening (3) for the switch (15) and an element (8) of an electrically conductive material having the shape of a closed loop is present between the panel (4) and the wall portion (2), by means of which element (8) the panel (4) is fastened to the wall portion (2) in an RF adhesion process.

3. An apparatus as claimed in claim 2 wherein the RF adhesion process takes place at a frequency of between 30 kHz and 50 kHz.

4. An apparatus as claimed in claim 2 wherein the element (8) is made of brass or nickel.

5. An apparatus as claimed in claim 2, wherein a second panel (18) is present which is fastened to the outside (17) of the wall portion (2), again by means of an element (19) of electrically conducting material in the shape of a closed loop and an RF adhesion process, which panel (18) has an operational surface (23) of a flexible material which lies opposite the membrane (13) with the actuator (14) of the panel (4) mentioned earlier, and which panel (18) covers the opening (11) for the switch (15) in the wall portion (2).

6. An apparatus as claimed in claim 1, wherein the RF adhesion process takes place at a frequency of between 30 kHz and 50 kHz.

7. An apparatus as claimed in claim 1, wherein the element (8) is made of brass or nickel.

8. An apparatus as claimed in claim 1, wherein the wall portion (2) has at least one opening (3) for accommodating a display.

* * * * *